(12) United States Patent
Watanabe

(10) Patent No.: US 6,496,272 B1
(45) Date of Patent: Dec. 17, 2002

(54) ILLUMINATOR FOR USE IN ELECTRONIC COMPONENT MOUNTING APPARATUS AND ELECTRONIC COMPONENT MOUNTING APPARATUS HAVING ILLUMINATOR

(75) Inventor: Mahito Watanabe, Yamagata (JP)

(73) Assignee: Yamagata Casio Co., Ltd., Higshine (JP)

(*) Notice: Subject to any disclaimer, the term of this patent is extended or adjusted under 35 U.S.C. 154(b) by 0 days.

(21) Appl. No.: 09/417,192

(22) Filed: Oct. 12, 1999

(30) Foreign Application Priority Data

Oct. 13, 1998 (JP) .......................................... 10-290491

(51) Int. Cl.$^7$ .......................... G01B 11/14; G01N 21/00
(52) U.S. Cl. ..................................... 356/614; 356/237.1
(58) Field of Search .............................. 356/614, 237.1, 356/240.1; 250/239, 216, 222.2, 223 R, 223 B, 559.46, 571, 572

(56) References Cited

U.S. PATENT DOCUMENTS

| 4,028,728 | A | * | 6/1977 | Sharp .......................... 358/106 |
| 4,893,223 | A | * | 1/1990 | Arnold ......................... 362/25 |
| 5,072,127 | A | * | 12/1991 | Cochran et al. ............. 250/572 |
| 5,739,525 | A | * | 4/1998 | Greve ..................... 250/227.11 |
| 5,923,772 | A | | 7/1999 | Fukuda et al. ............... 381/141 |

OTHER PUBLICATIONS

Patent Abstracts of Japan, vol. 1995, No. 10, Nov. 30, 1995, Abstract of JP 07 174532 A, Jul. 14, 1995.
Patent Abstracts of Japan, vol. 1998, No. 06, Apr. 30, 1998, Abstract of JP 10 048504 A, Feb. 20, 1998.
Patent Abstracts of Japan, vol. 017, No. 583, Oct. 22, 1993, Abstract of JP 05 175697 A, Jul. 13, 1993.
Patent Abstracts of Japan, vol. 1998, No. 04, Mar. 31, 1998, Abstract of JP 09 321494 A, Dec. 12, 1997.
Patent Abstracts of Japan, vol. 018, No. 148, Mar. 11, 1994, Abstract of JP 05 327292 A, Dec. 10, 1993.
Patent Abstracts of Japan, vol. 1998, No. 02, Jan. 30, 1998, Abstract of JP 09 282444 A, Oct. 31, 1997.

* cited by examiner

*Primary Examiner*—Michael P. Stafira
(74) *Attorney, Agent, or Firm*—Frishauf, Holtz, Goodman & Chick, P.C.

(57) ABSTRACT

An illuminator includes: a first cylindrical member with a mirror-like inner surface formed to facilitate light reflection; a flat plate member having an aperture in its center; LEDs with trimmed distal ends and arranged in a circle along the periphery of the aperture; LEDs with trimmed distal ends and arranged in a circle along a circumferential direction of the first cylindrical member so as to be located on a lengthwise middle part of the inner surface of the cylindrical member; a second cylindrical member having an engagement portion engaged with the cylindrical member, LEDs with trimmed distal ends and arranged in a circle along a circumferential direction of the engagement portion; and a ring-shaped semitransparent diffusion plate. The illuminators illuminate a to-be-mounted component with light having a directivity.

25 Claims, 15 Drawing Sheets

ILLUMINATOR FOR USE IN ELECTRONIC COMPONENT MOUNTING APPARATUS AND ELECTRONIC COMPONENT MOUNTING APPARATUS HAVING ILLUMINATOR

BACKGROUND OF THE INVENTION

1. Field of the Invention

The present invention relates to an illuminator, which radiates light onto a to-be-mounted component conveyed by the head of a component mounting apparatus, in order to detect the posture and position of the electronic component, and also relates to the component mounting apparatus with the illuminator.

2. Description of the Related Art

A known component mounting apparatus (mounter) has a head which is movable in X-, Y- and Z-directions and which holds an electronic component by suction and conveys the electronic component to a predetermined mounting position. In this type of mounter, however, deviations can occur in the position and posture of the electronic component. In consideration of this, the electronic component held by the head is photographed with a camera in order to recognize the position and posture of the electronic component, and the operation of the head is controlled and corrected to mount the electronic component in its predetermined position.

Conventional mounters adopt various ideas for enabling the camera to photograph the electronic component with improved precision. Some mounters employ an illuminator to illuminate the electronic component held by the head with light.

A conventional illuminator is square in cross section and includes a case 520 having inner surfaces on which light sources 540 and light reflectors 580 are arranged as illustrated in FIGS. 14A and 14B, for example. A to-be-mounted electronic component 1 located above the illuminator is illuminated with light emitted from the light sources 540.

According to the above illuminator, however, when illuminating an electronic component having burnished leads 1b with light as illustrated in FIG. 15, the light radiated onto the leads 1b is reflected in a direction different from that of a camera 650, under which condition the leads 1b of the electronic component do not uniformly glisten in white, entailing the possibility that any curved portions of the leads 1b may be photographed partially black.

SUMMARY OF THE INVENTION

The present invention has been made in consideration of the above-described circumstances, and an object thereof is to provide an illuminator which can appropriately illuminate a to-be-mounted component with light, and a component mounting apparatus having such illuminators.

Another object of the present invention is to provide an illuminator which can improve the accuracy of recognition of the position and posture of a to-be-mounted component, and a component mounting apparatus having such illuminators.

According to the first aspect of the present invention, there is provided an illuminator for illuminating a to-be-mounted component with light, comprising:

light sources; and a reflector including a cylindrical member with a mirror-like inner surface by which light emitted from the light sources is reflected and radiated onto the to-be-mounted component.

According to the illuminator of the present invention, the light incident from the light source is reflected by the inner surface of the cylindrical member and radiated onto the to-be-mounted component with an intensity same as that of the incident light. Therefore, an image of the to-be-mounted component and background thereof with a high contrast can be obtained. Thus, the posture and position of the to-be-mounted components can be recognized with a high precious. Further, images of the parts of the to-be-mounted component, for example, images of electrodes are clear and precise. Thus, the presence or absence of any damaged/broken part of the electrode, for example, can be easily detected.

It is desirable that the inner surface of the cylindrical member may reflect the light emitted from the light sources and radiate light having a directivity, onto the to-be-mounted component.

If directivity of the light is too high, the to-be-mounted component can not be illuminated preferably. On the other hand, directivity of the light is too low, the contrast of the image is low. According to the this structure, the light is reflected by the miller-like inner surface of the cylindrical member and radiated on the to-be-mounted components from many directions with an intensity same as that of the incident light. Therefore, light having directivity are irradiated on the to-be-mounted components without unevenness, resulting in an image of the components and background with high contrast. Thus, the posture and position of the to-be-mounted components can be recognized with a high precious. To obtain the light having directivity, ratio of diameter to length (diameter/length) of the cylindrical member is, for example, 3/12 to 10/12, more specifically, 5/12 to 10/12, and further 7/12 to 9/12.

It is desirable that the cylindrical member leads, to the to-be-mounted component, the light emitted from the light sources, while reflecting the light by the inner surface; and the light sources are arranged inside the cylindrical member and emit light in an inner space defined by the cylindrical member.

According to this structure, the light having directivity is irradiated onto the to-be-mounted components without unevenness. Therefore, an image of the components and background with a high contrast can be obtained.

It is desirable that the cylindrical member has a first end and a second end; and the light sources include
first light sources forming a first light source group and arranged at the first end of the cylindrical member which is closer to the to-be-mounted component than the second end of the cylindrical member,
second light sources forming a second light source group and arranged at the second end of the cylindrical member, and
third light sources forming a third light source group and arranged between the first and second ends of the cylindrical member.

According to this structure, the light rays radiated at different angles from the first to third light sources are radiated onto the to-be-mounted components without unevenness with directivity by reflected on the inner surface of the cylindrical member. Therefore, an image of the to-be-mounted components and background can be obtained. Thus, the posture and position of the to-be-mounted components can be recognized with a high precious.

The cylindrical member is circular in cross section, for example. In this case, for example, the first, second and third light sources are arranged in a circumferential direction of the cylindrical member.

According to this structure, the light rays emitted from the first, second and third light sources are radiated onto the to-be-mounted components at various angles throughout the whole circumference thereof. Therefore, the light is irradiated onto the to-be-mounted components without unevenness, and the form and position of the to-be-mounted components can be recognized with a high precious.

The cylindrical member covers, for example, parts of the first light sources which face the second end of the cylindrical member, in order to prevent light from being emitted toward the second end of the cylindrical member from the first light sources.

According to this structure, the light rays are prevented from being radiated toward the second end from the first light sources and from being unnecessarily radiated onto the components. Thus, in a case where the to-be-mounted components are, for example, BGA type semiconductor chips, the presence or absence of damaged/broken part in their ball-shaped surface can be easily detected, because the ball-shaped surfaces are glistening annularly (in a doughnut shape).

The cylindrical member has a bottom which covers at least a part of an opening at the second end of the cylindrical member, and the second light sources are arranged on the bottom.

A diffusion member in a form of a flat plate, which diffuses light emitted from the second light sources, is arranged almost perpendicular to an axis of the second cylindrical member and between the first light source group comprising the second light sources and the third light source group comprising the third light sources.

According to this structure, the light rays radiated from the third light sources arranged on the bottom are diffused by the diffusion member so as to be radiated onto the to-be-mounted components. Therefore, in a case where the light rays having strong brightness are radiated onto the to-be-mounted components, the light rays are emitted to a light-outgoing portion thereof, and thus the form and the posture of the to-be-mounted components are recognized with a high precious.

The first light sources may be detachably attached to the reflection member. According to this structure, the first light sources may be attached to or removed from the reflection member in accordance with the shape or material of the to-be-mounted component, so that the amount or angle of lights to be irradiated onto the to-be-mounted component is adjustable.

At least one of the first, second and third light source group may comprise a plurality of LEDs having distal ends trimmed to diffuse the illumination lights. According to this structure, since the LEDs have the trimmed distal ends, the illumination lights will be diffused. Thus, the light source can irradiate the lights onto the to-be-mounted component without unevenness.

In order to accomplish the above object, a component mounting apparatus according to a second aspect of the present invention comprises a head and illuminators, and which causes the head to suck up and hold a to-be-mounted component, causes the illuminators to illuminate the to-be-mounted component with light, detects a posture and position of the to-be-mounted component, controls the head in accordance with the detected posture and position of the to-be-mounted component, and mounts the to-be-mounted component held by the head in a predetermined position, each of the illuminators comprises:

light sources; and a reflector including a cylindrical member with a mirror-like inner surface by which light emitted from the light sources is reflected and radiated having a predetermined directivity onto the to-be-mounted component.

According to the component mounting apparatus, diffused lights from the first, second and third light sources each having different incident angle are reflected by the reflection member without decreasing the strength, and the lights having stronger directivity reach the component set near the upper end. Therefore, the lights are irradiated onto the to-be-mounted component without unevenness, thus, the components and the background are highly contrasted. As a result, a posture and position of the to-be-mounted component can be detected with higher accuracy.

The light sources comprise first light sources arranged in a circle at the upper end of the cylindrical member, second light sources arranged in a circle at the lower end of the cylindrical member, and third light sources arranged in a circle between the upper and lower ends of the cylindrical member.

According to the component mounting apparatus, the first, second and third light sources arranged around the to-be-mounted component irradiate lights each having different incident angle onto the component. Thus, the lights are irradiated onto the component without unevenness. As a result, a posture and position of the component can be detected with higher accuracy.

The cylindrical member may cover parts of the first light sources which face the lower end of the cylindrical member, in order to prevent from being emitted toward the lower end of the cylindrical member from the first light sources.

This structure prevents the component from being irradiated by extra lights. That is, the lights irradiated toward the lower end of the cylindrical member from the first light sources are prevented from being reflected by the other end. Therefore, even if the to-be-mounted component is, for example, a BGA type semiconductor chip, damages or failures on a ball can be easily detected because the surface of the ball is illuminated circular.

At least one of the first, second and third light source group may comprise a plurality of LEDs having distal ends trimmed to diffuse the illumination lights. According to this structure, since the LEDs have the trimmed distal ends, the illumination lights will be diffused. Thus, the light source can irradiate the lights onto the to-be-mounted component without unevenness.

A nozzle of the head may comprise, for example, a conic reflector which reflect lights, which are irradiated onto the nozzle by the illuminator, so that the direction of the reflected lights differs from the direction from the illuminator to the nozzle.

According to the third aspect of the present invention, there is provided a plurality of illuminators, used in a component mounting apparatus comprising a head which sucks up and holds a to-be-mounted component, for illuminating the to-be-mounted component held by the head with light, each of the plurality of illuminators comprising:

a cylindrical member with a mirror-like inner surface formed to facilitate light reflection and by which light is reflected and radiated having a directivity onto the to-be-mounted component;

a flat plate member having an aperture formed in a center thereof and covering a periphery of an opening at one end of the cylindrical member;

LEDs arranged in a circle along the periphery of the opening;

a ring-shaped semitransparent diffusion plate which diffuses light emitted from the LEDs;

LEDs arranged in a circle along a circumferential direction of the cylindrical member so as to be located on a lengthwise middle part of the inner surface of the cylindrical member;

an engagement portion engaged with the cylindrical member; and

LEDs arranged in a circle along a circumferential direction of the engagement portion and having distal ends trimmed substantially coplanar with the inner surface of the cylindrical member.

According to the fourth aspect of the present invention, there is provided an illuminating method for illuminating a to-be-mounted component, sucked up and held by a head of a component mounting apparatus, with light emitted from illuminators, in order to recognize a posture and position of the to-be-mounted component through use of a camera, the method comprising the steps of:

reflecting light emitted from at least one light source by a mirror-like inner surface of a cylindrical member; and radiating the light, reflected having a directivity by the inner surface of the cylindrical member, onto the to-be-mounted component.

The cylindrical member leads to the to-be-mounted component, the light emitted from the at least one light source, while reflecting the light by the inner surface of the cylindrical member; and the at least one light source is arranged inside the cylindrical member and emits light in an inner space defined by the cylindrical member.

BRIEF DESCRIPTION OF THE DRAWINGS

These objects and other objects of the present invention, as well as the advantages of the present invention, will become more apparent upon reading of the following detailed description and the accompanying drawings in which.

DETAILED DESCRIPTION OF THE PREFERRED EMBODIMENT

An embodiment of the present invention will now be described with reference to the accompanying drawings.

Figure 1A:
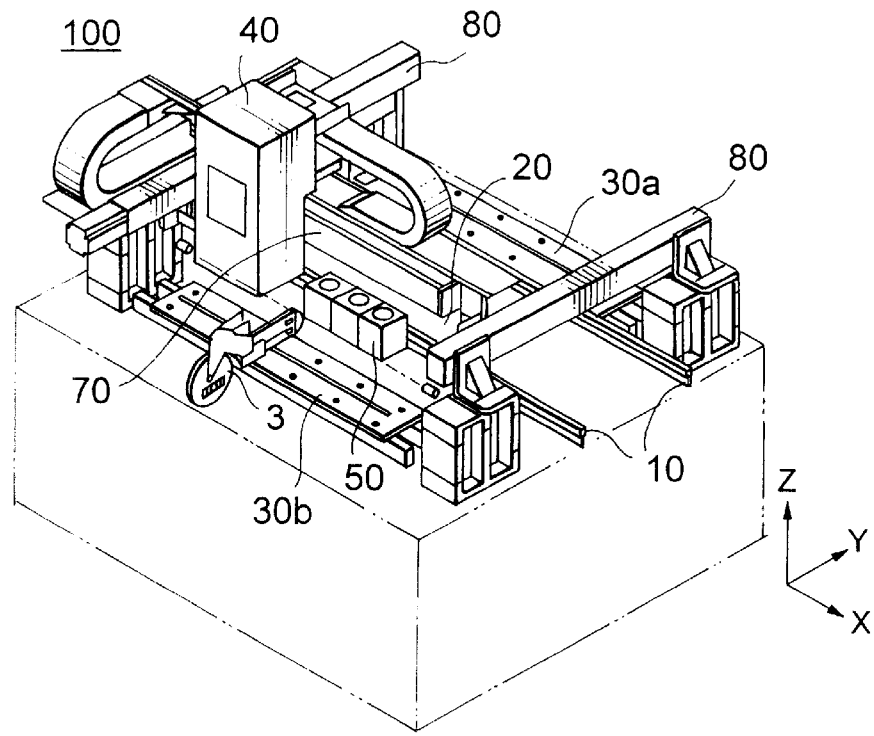
FIG. 1A is a perspective view of a component mounting apparatus according to an embodiment of the present invention.
Figure 1B:
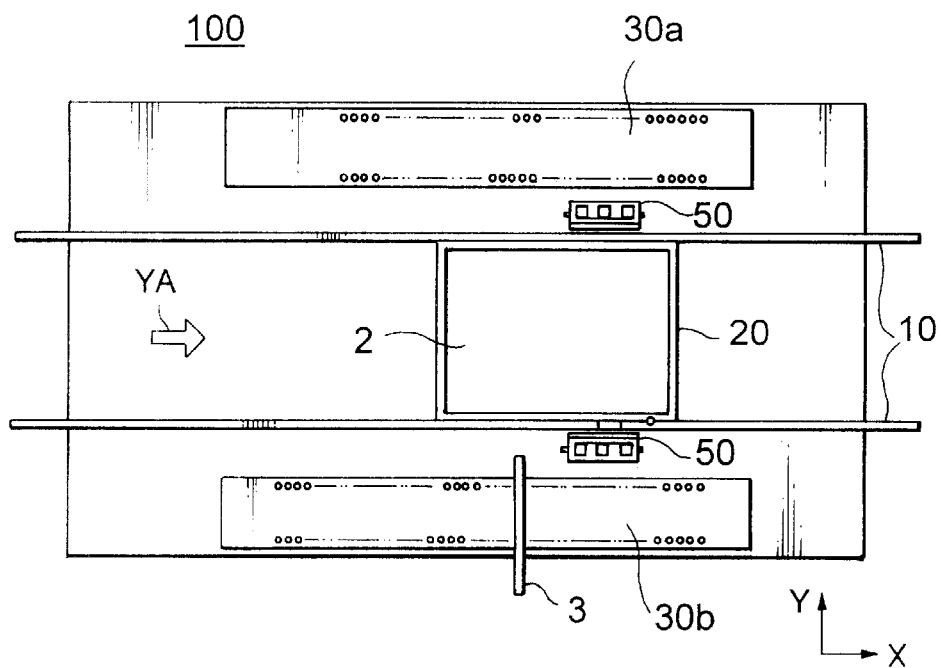
FIG. 1B is a plan view of the component mounting apparatus illustrated in FIG. 1A.

As illustrated in FIGS. 1A and 1B, a component mounting apparatus according to an embodiment of the present invention has a conveyor 10, a supporting member 20 which supports a substrate on which components are to be mounted, tables 30a and 30b on which a cassette 3 is placed, a work tower 40 which mounts the components in their target positions, a parts recognition unit 50 which recognizes the postures and positions of the components to be mounted, an X-axial section 70 and a Y-axial section 80 which move the work tower 40 in X- and Y-axial directions, respectively.

The conveyor 10, having a pair of conveyor belts and guide rails for guiding the substrate, conveys the substrate in the direction shown by arrow YA.

When mounting a to-be-mounted component on the substrate 2, the supporting member 20 provided between the conveyor belts temporarily supports the substrate 2, as illustrated in FIG. 1B.

The tables 30a and 30b are plate-shaped, and the cassette 3 for the supply of the components to be mounted is placed on the table 30a or 30b.

The X-axial section 70, including a linear guide, a ball screw, an X-axial motor 72 (FIG. 6), etc., moves the work tower 40 in the X-axial direction.

The Y-axial section 80, including a linear guide, a ball screw, a Y-axial motor 82 (FIG. 6), etc., moves the work tower 40 in the Y-axial direction.

Figure 2:
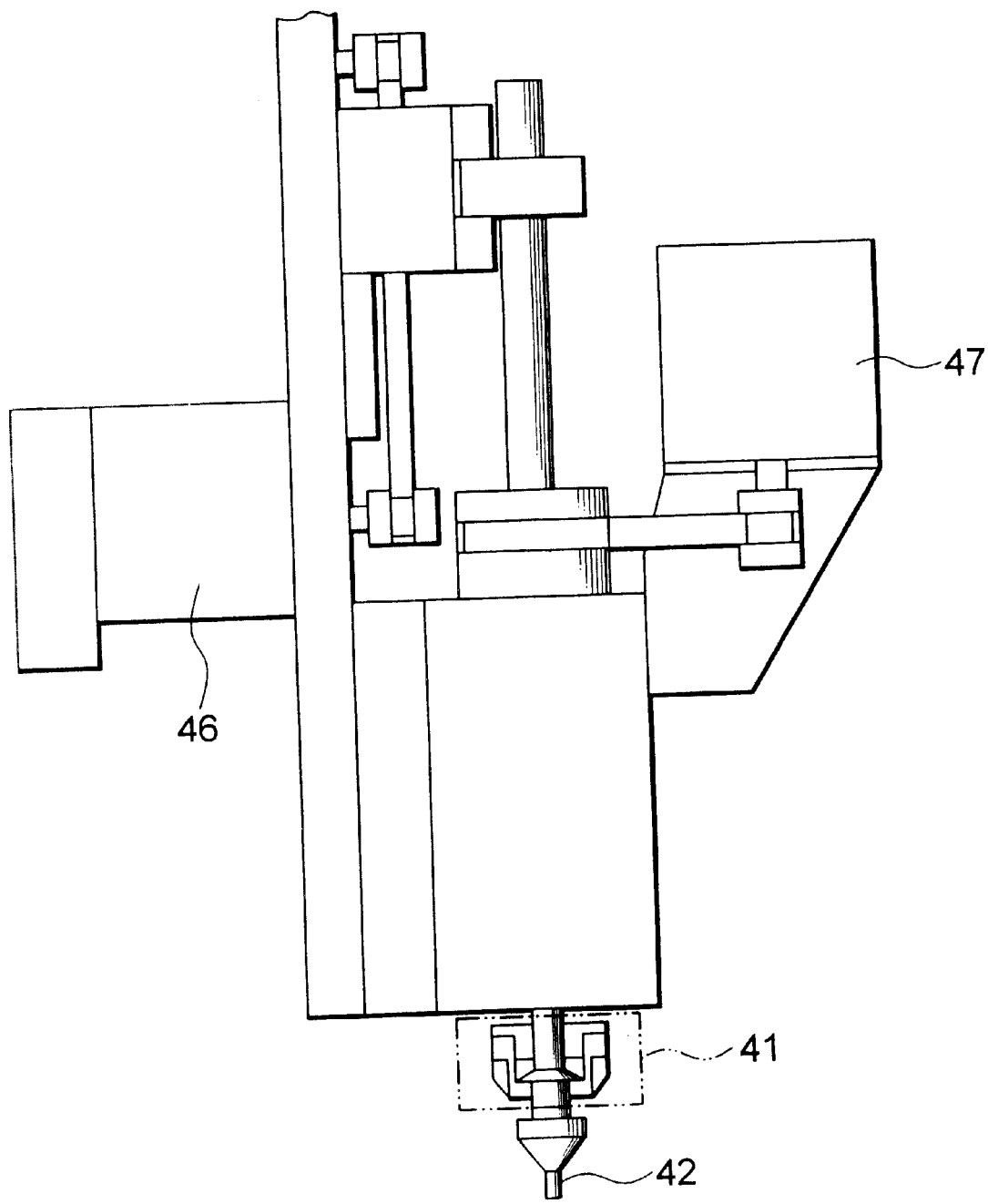
FIG. 2 is a partial sectional view of a work tower which the component mounting apparatus illustrated in FIGS. 1A and 1B comprises.

As illustrated in FIG. 2, the work tower 40 has a work head 41 with a nozzle 42 attached thereto for sucking up and holding a to-be-mounted component, a Z-axial motor 43 which moves the work head 41 in a Z-axial direction, and a rotational motor 44 which rotates the work head 41 within an X-Y plane. The work head 41 detachably holds the nozzle 42 and moves in X, Y, and Z directions for sucking up and moving a to-be-mounted component. Desirably, the work head 41 has a flat lower surface and is mat finished, for example, dull-finished and mat-black-finished, in order to weaken the reflected lights.

Figure 3A:
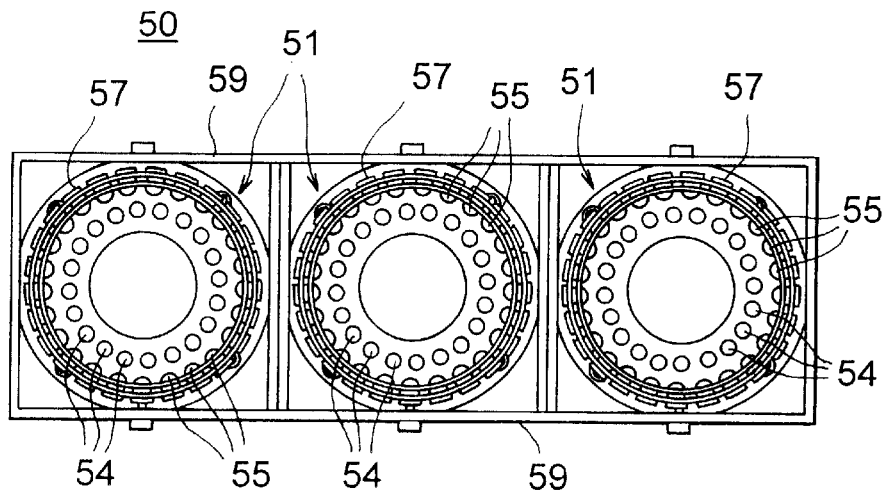
FIG. 3A is a plan view of a component recognition unit which the component mounting apparatus illustrated in FIGS. 1A and 1B comprises.
Figure 3B:
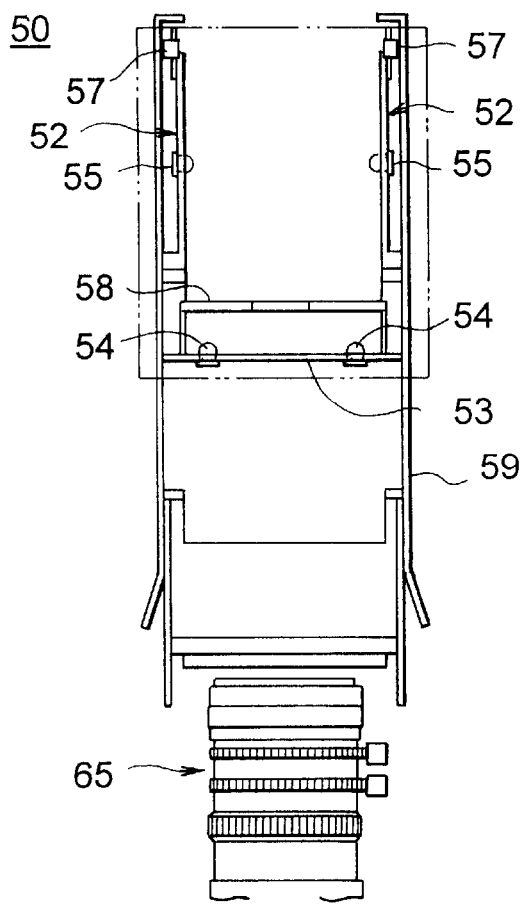
FIG. 3B is a partial sectional view of the component recognition unit which the component mounting apparatus illustrated in FIGS. 1A and 1B comprises.

As illustrated in FIGS. 3A and 3B, the component recognition unit 50 includes illuminators 51 which illuminate the to-be-mounted component held by the nozzle 42 with light, a cover 59 which encloses the illuminators 51, and a camera 65 which takes in, as an image, the posture, position and shape of the to-be-mounted component illuminated with the light emitted from the illuminators 51.

Figure 4:
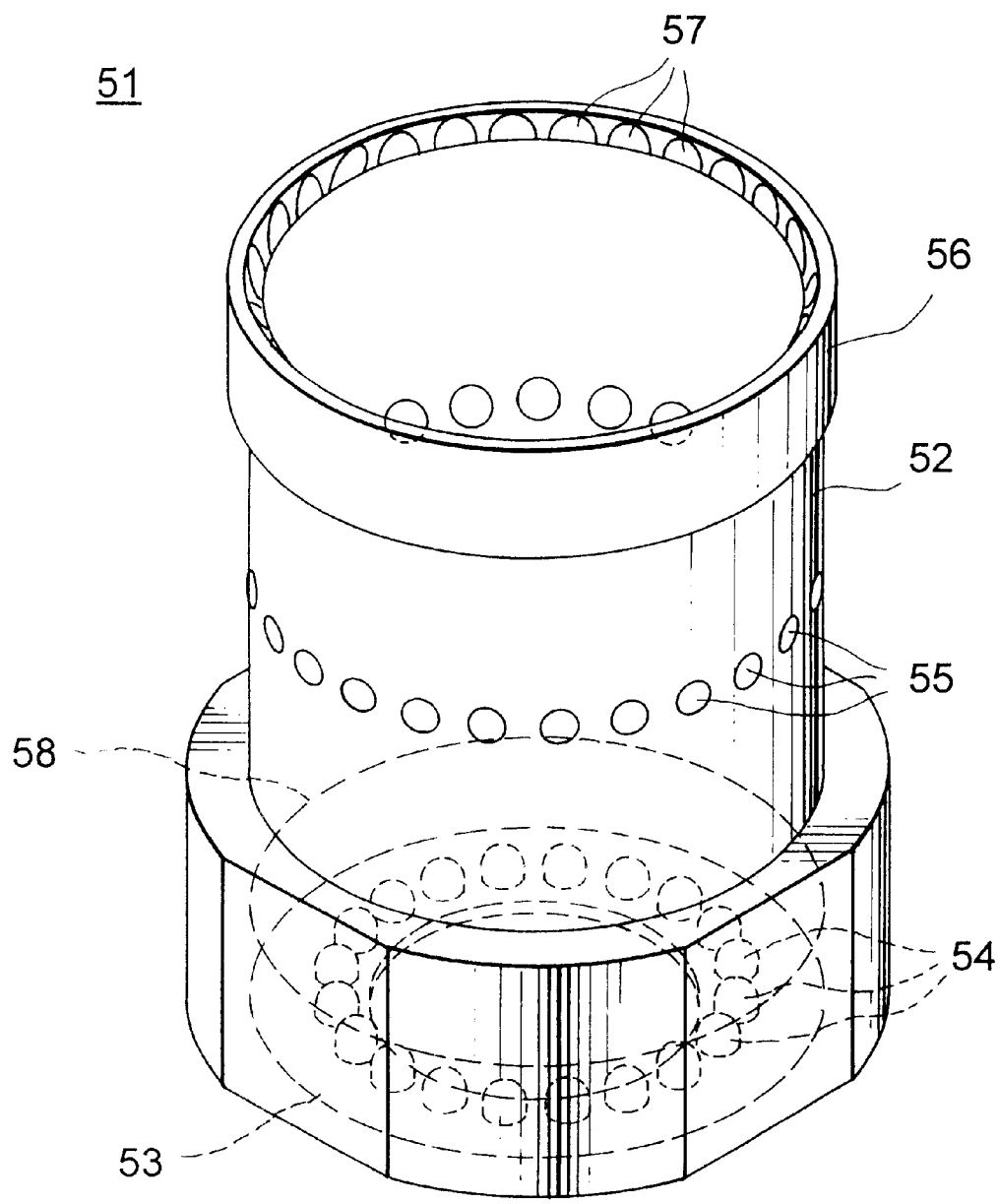
FIG. 4 is a perspective view of illuminators which the component recognition unit illustrated in FIGS. 3A and 3B comprises.
Figure 5A:
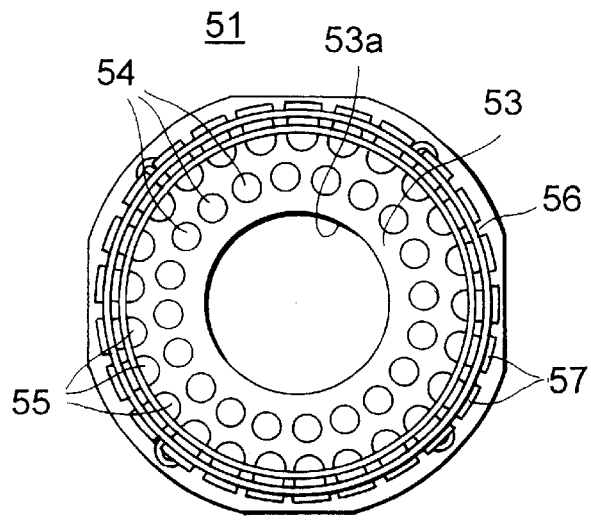
FIG. 5A is a plan view of one of the illuminators which the component recognition unit illustrated in FIGS. 3A and 3B comprises.
Figure 5B:
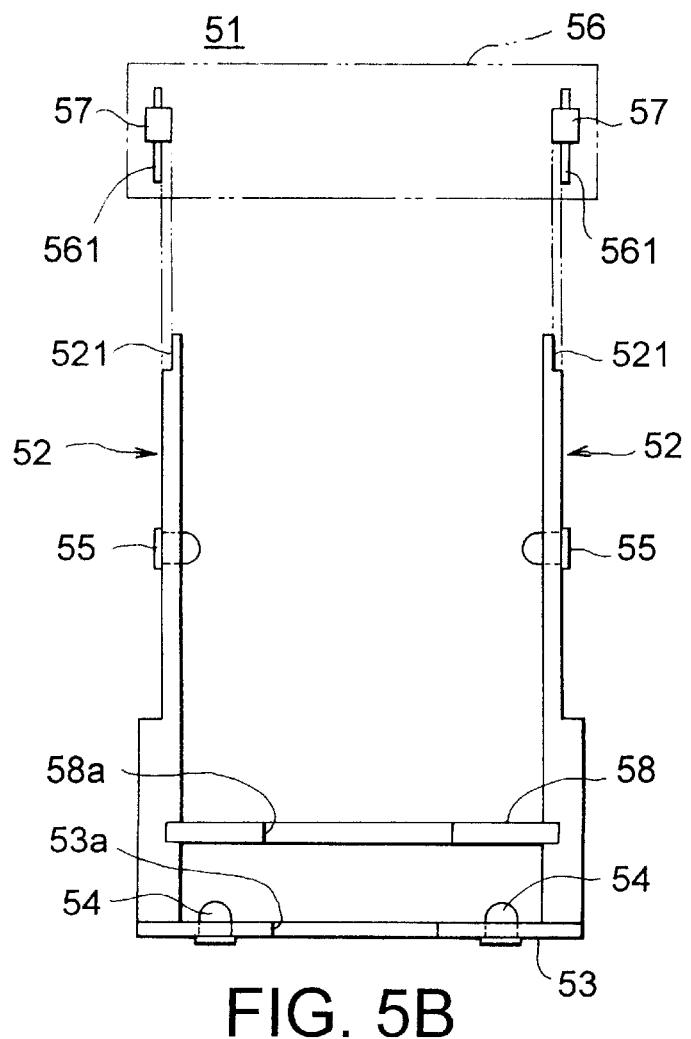
FIG. 5B is a sectional view of one of the illuminators which the component recognition unit illustrated in FIGS. 3A and 3B comprises.

As illustrated in FIGS. 4, 5A and 5B, each of the illuminators 51 has a first cylindrical member 52, a flat plate member (bottom) 53 covering a part of one end of the first cylindrical member 52, a plurality of light emitting diodes (LEDs) 54 arranged in the circumferential direction of the bottom 53, a plurality of LEDs 55 provided on the inner surface of the first cylindrical member 52 in the circumferential direction thereof, a second cylindrical member 56 detachably engaged with the first cylindrical member 52, a plurality of LEDs 57 arranged in the circumferential direction of the second cylindrical member 56, and a diffusion plate 58 which diffuses light emitted from the LEDs 54.

The first cylindrical member 52 is almost circular in cross section, and its inner surface is a mirror-like surface which reflects light radiated from the LEDs 54, 55 and 57. It is preferred that the "mirror-like" surface be a surface which has been subjected to a mirror treatment. However, the mirror-like surface is not limited to such a surface, and the state "mirror-like" described herein implies the state of reflecting almost all incoming light rays, diffusing them a little. For example, such a surface as can reflect a neighborhood object will suffice as the mirror-like surface. In the case of forming the first cylindrical member 52 by processing a metal plate which is made of aluminum or the like, the metal plate needs to have flat surfaces.

The first cylindrical member 52 has a coupling portion 521 which abuts against the LEDs 57 arranged at the second cylindrical member 56 along the outer circumferential surface of the light-outgoing end portion of the first cylindrical member 52.

The flat plate member 53, covering a part of an opening at one end of the first cylindrical member 52, comprises a ring-shaped flat plate member having an aperture 53a formed in the center thereof in order to guide, to the camera 65, light reflected from the to-be-mounted component.

The LEDs (second light sources) 54 are arranged in a circle around the aperture 53a of the flat plate member 53, in the state wherein the LEDs 54 are separated from the periphery of the aperture 53a by such an amount that light emitted from the LEDs 54 does not directly enter the camera 65. The LEDs 54 have distal ends trimmed (rounded off) so as to emit illumination light in a diffused state.

The LEDs (third light sources) 55 are arranged in a circle (within an imaginary plane perpendicular to the axis of the first cylindrical member 52) along the circumferential direction of the first cylindrical member 52 so as to be located on a lengthwise middle part of the inner surface of the first cylindrical member 52. The LEDs 55 also have distal ends trimmed (rounded off) so as to emit illumination light in a diffused state.

The second cylindrical member 56 includes an engagement portion 561, shaped in a cylinder slightly larger in diameter than the first cylindrical member 52, and the LEDs (first light sources) 57 arranged in a circle along the circumferential direction of the engagement portion 561.

The engagement portion 561 is detachably engaged with the outer periphery of the first cylindrical member 52.

The LEDs 57 abut fixedly against the coupling portion 521 of the first cylindrical member 52. Under this condition, the first cylindrical member 52 engaged with the engagement portion 561 covers those parts of the LEDs 57 which face the camera 65, so that no light is emitted toward the camera 65 from the LEDs 57. The LEDs 57 have distal ends trimmed so as to emit light in a diffused state.

The diffusion plate 58, comprising a ring-shaped semi-transparent flat plate member, diffuses the light emitted from the LEDs 54. The diffusion plate 58 has an aperture 58a formed in the center thereof in order to guide, to the camera 65, the light reflected from the to-be-mounted component.

As seen from FIG. 3B, the camera 65 has an optical axis which is in alignment with an imaginary line connecting the to-be-mounted component held by the nozzle 42 and the center of the aperture 53a formed in the flat plate member 53, and takes in an image of the to-be-mounted component illuminated with the light emitted from the illuminators 51.

Figure 6A:
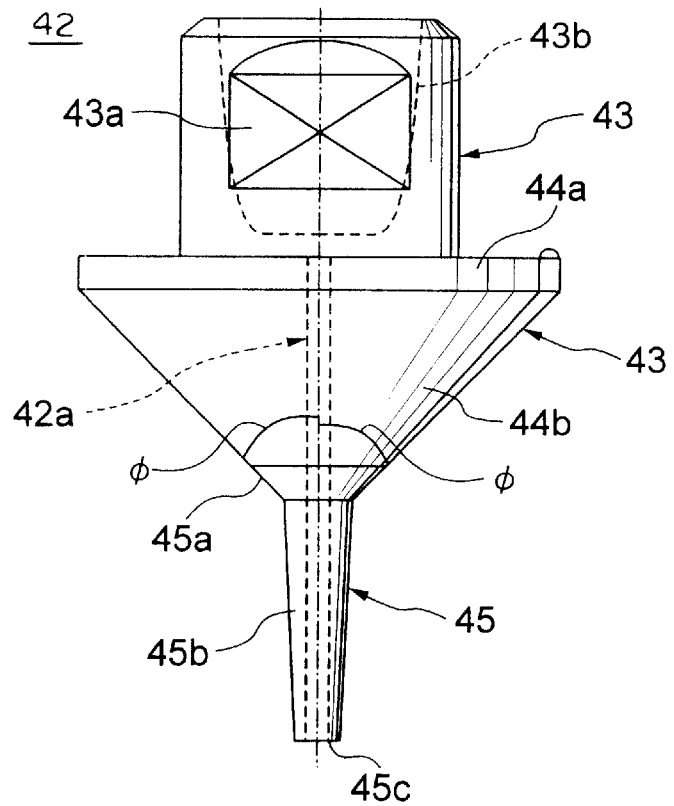
FIGS. 6A and 6B are side and plain views of a nozzle, respectively.
Figure 6B:
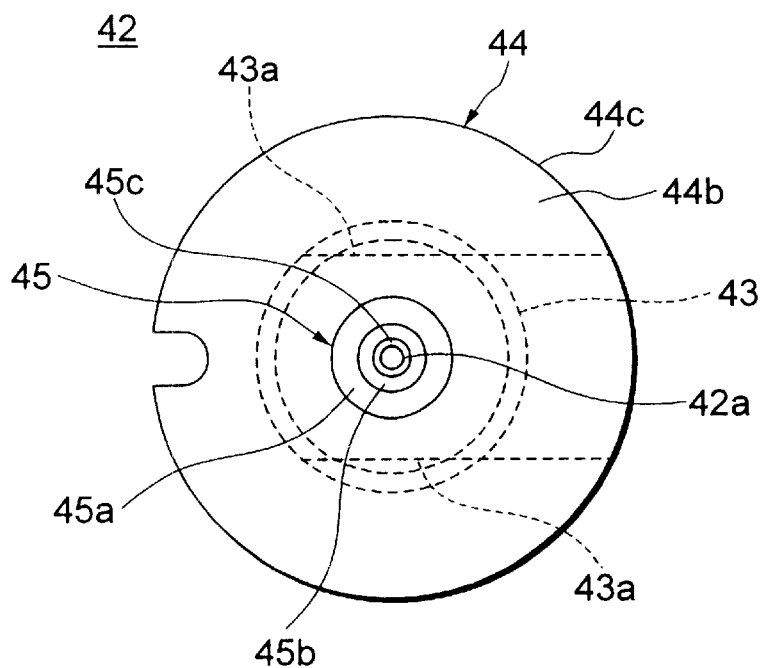

As shown in FIGS. 6A and 6B, the nozzle 42 comprises a cylindrical attachment unit 43 to be attached to the pipe 411 in the operation head 41, a reflector 44 which reflects lights from the illuminator 51 in the direction which differs from the direction from the illuminator 51 to the reflector 44, a component holding section 45 which holds a component with a negative pressured air from the pipe 411, and an air vent pipe 42a for the negative pressured air prepared for attracting the component.

The cylindrical attachment unit 43 comprises a recessed portion 43a to be latched by the chuck 412, and a mortise 43b to be mate with the pipe 411.

The reflector 44 which is fixed on the attachment unit 43 comprises a cylinder section 44a whose diameter is larger than that of the attachment unit 43, and a cone section 44b.

An angle between a cone surface and a vertical axis is set to φ which is smaller than 45 degrees so as to avoid lights from downward (more precisely, from the latter-described illuminator 51 in the component recognizer 50) from being reflected downward (more precisely, toward the camera 65 in the component recognizer 50). The outer surface of the cone section 44b is mat finished such as dull finish and mat black finish, in order to weaken the reflected lights.

The component holding section 45 comprises a fixing member 45a and a contact needle 45b.

The fixing member 45a is formed similar to the reflector 44 but smaller than it, and fixes the component attracting section 45 onto the cone section 44b.

The contact needle 45b has cylindrical shape but tapered to a contact portion 45c at a tip of the contact needle 45b.

Figure 7:
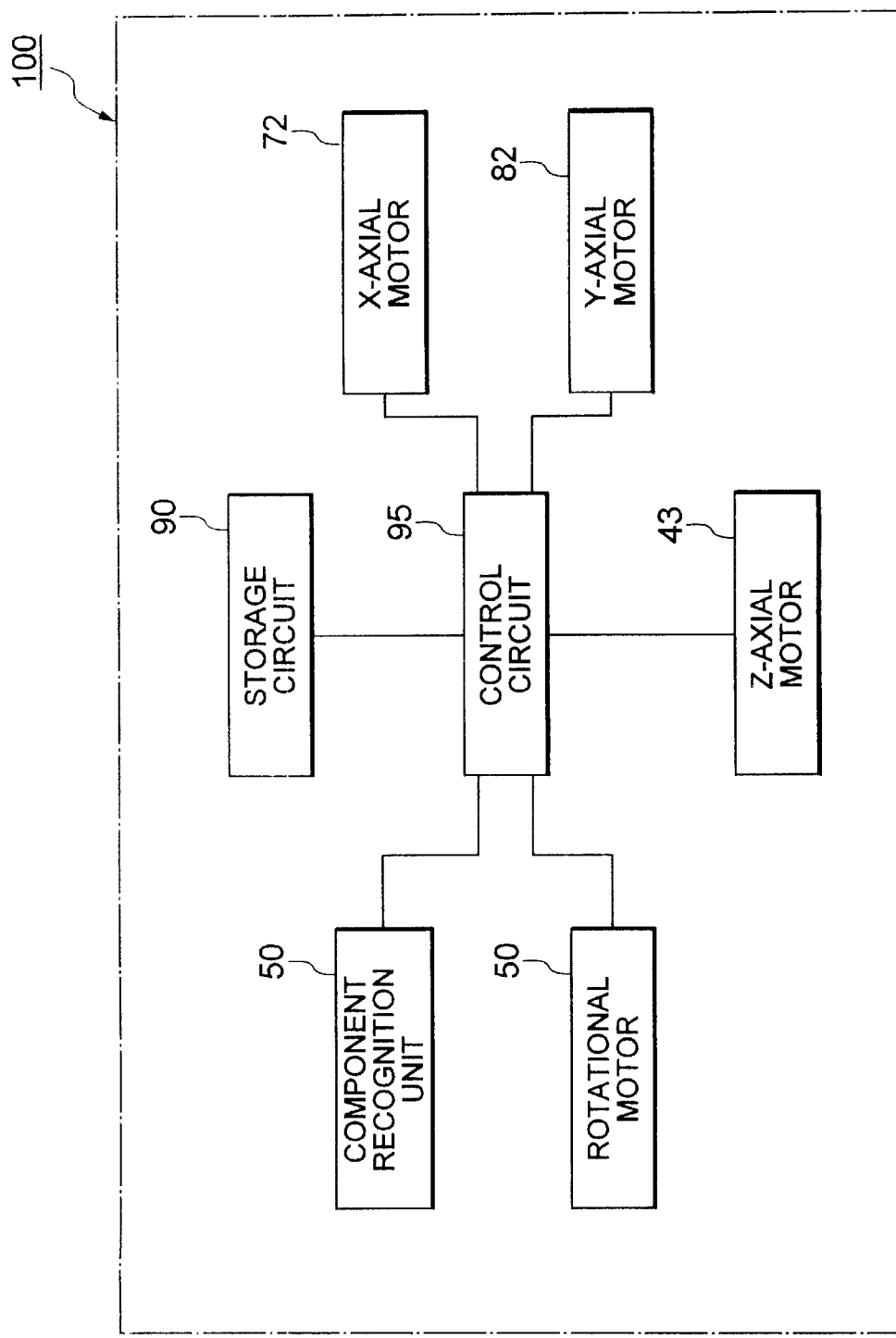
FIG. 7 is a block diagram showing the circuit structure of the component mounting apparatus illustrated in FIGS. 1A and 1B.

As illustrated in FIG. 7, the component mounting apparatus 100 includes a storage circuit 90 and a control circuit 95, in addition to the component recognition unit 50, which has the illuminators 51 and the camera 65, the X-axial motor 72, the Y-axial motor 82, the Z-axial motor 43 and the rotational motor 44 mentioned previously.

The storage circuit 90 stores data representing the correct posture, position and shape of the to-be-mounted component held by the nozzle 42, as well as an operation program which the control circuit 95 executes to mount on the substrate 2 the component arranged at the cassette 3.

While controlling the X-axial motor 72, the Y-axial motor 82, the Z-axial motor 43 and the rotational motor 44 in accordance with the operation program stored in the storage circuit 90, the control circuit 95 causes the nozzle 42 to suck up and hold the component arranged at the cassette 3 placed on the table 30a or 30b, and conveys the component held by the nozzle 42 in order to mount it in the target position on the substrate 2.

Furthermore, the control circuit 95 causes the component recognition unit 50 to perform a component recognizing operation which will be described later, and corrects the position of the nozzle 42 before mounting the component in the target position. Moreover, the control circuit 95 controls the turning ON and OFF of the illuminators 51 and the photographing operation of the camera 65, in synchronization with the component mounting operation of the component mounting apparatus 100.

The operation of the component mounting apparatus 100 according to an embodiment of the present invention will now be described with reference to the drawings.

In the case of mounting the to-be-mounted component on the substrate 2, the support member 20 supports the substrate 2 while being conveyed by the conveyor 10 in the direction shown by arrow YA. The cassette 3 holding the to-be-mounted component, or a semiconductor chip 1, is present on the table 30b.

When mounting on the substrate 2 the semiconductor chip 1 arranged at the cassette 3 under the above-described circumstances, the control circuit 95 controls the X-axial motor 72, the Y-axial motor 82 and the Z-axial motor 43 in accordance with the operation program stored in the storage circuit 90, and positions the nozzle 42 above the semiconductor chip 1.

Having positioned the nozzle 42 above the semiconductor chip 1, the control circuit 95 moves the nozzle 42 downward while controlling the Z-axial motor 43, causes the nozzle 42 to suck up and hold the semiconductor chip 1, and moves the nozzle 42 upward. Following this, the control circuit 95 controls the nozzle 42 so that it moves to a location above the component recognition unit 50, while holding the semiconductor chip 1.

Figure 8:
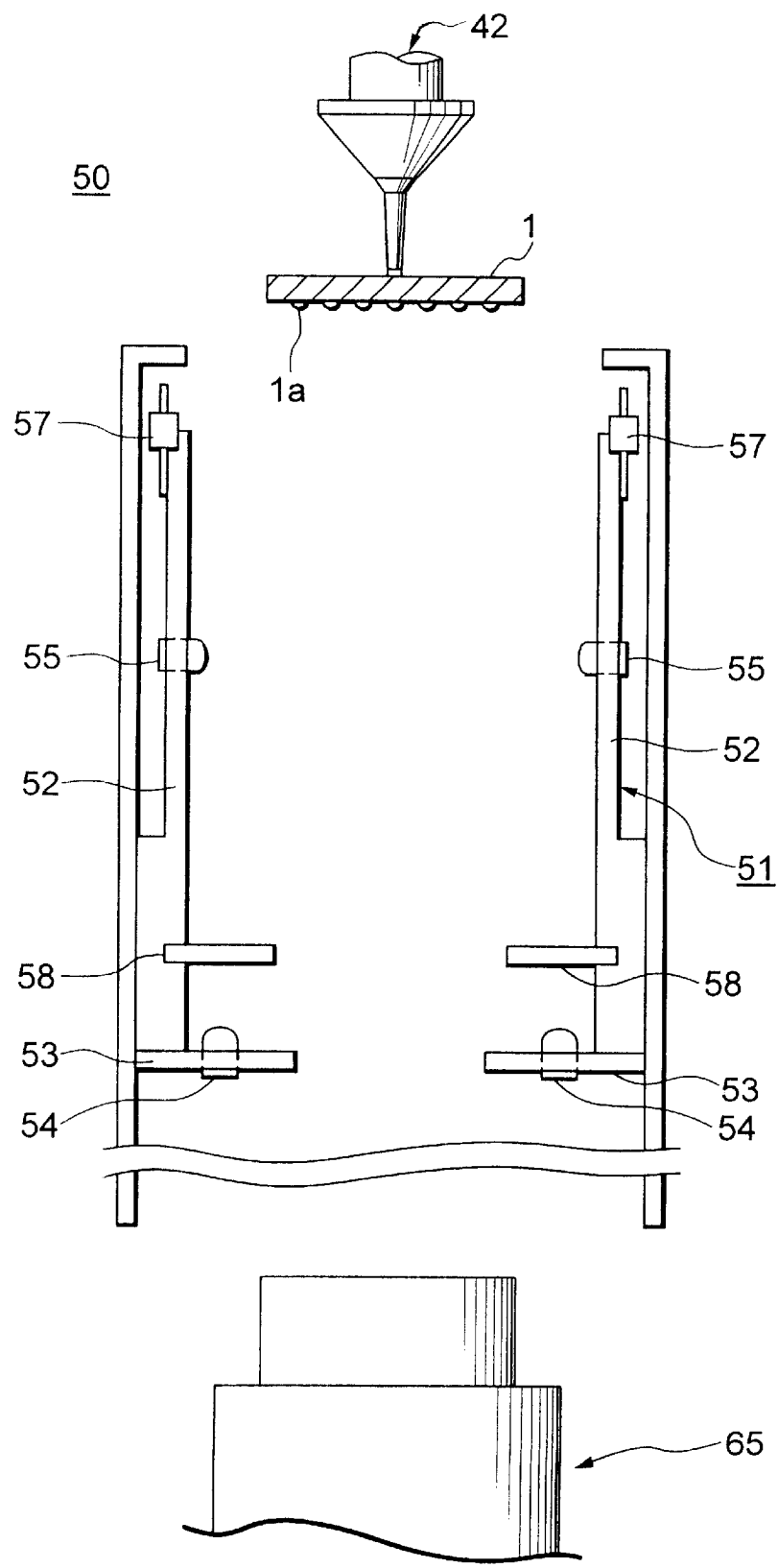
FIG. 8 is a sectional view of the component recognition unit in the state wherein a BGA type semiconductor chip is arranged above the component recognition unit.

Having controlled the nozzle 42 so as to move to a location above the component recognition unit 50 as illustrated in FIG. 8, the control circuit 95 initiates a component recognizing process for detecting how much the posture and position of the to-be-mounted component held by the nozzle 42 deviate from the correct posture and position.

Figure 9:
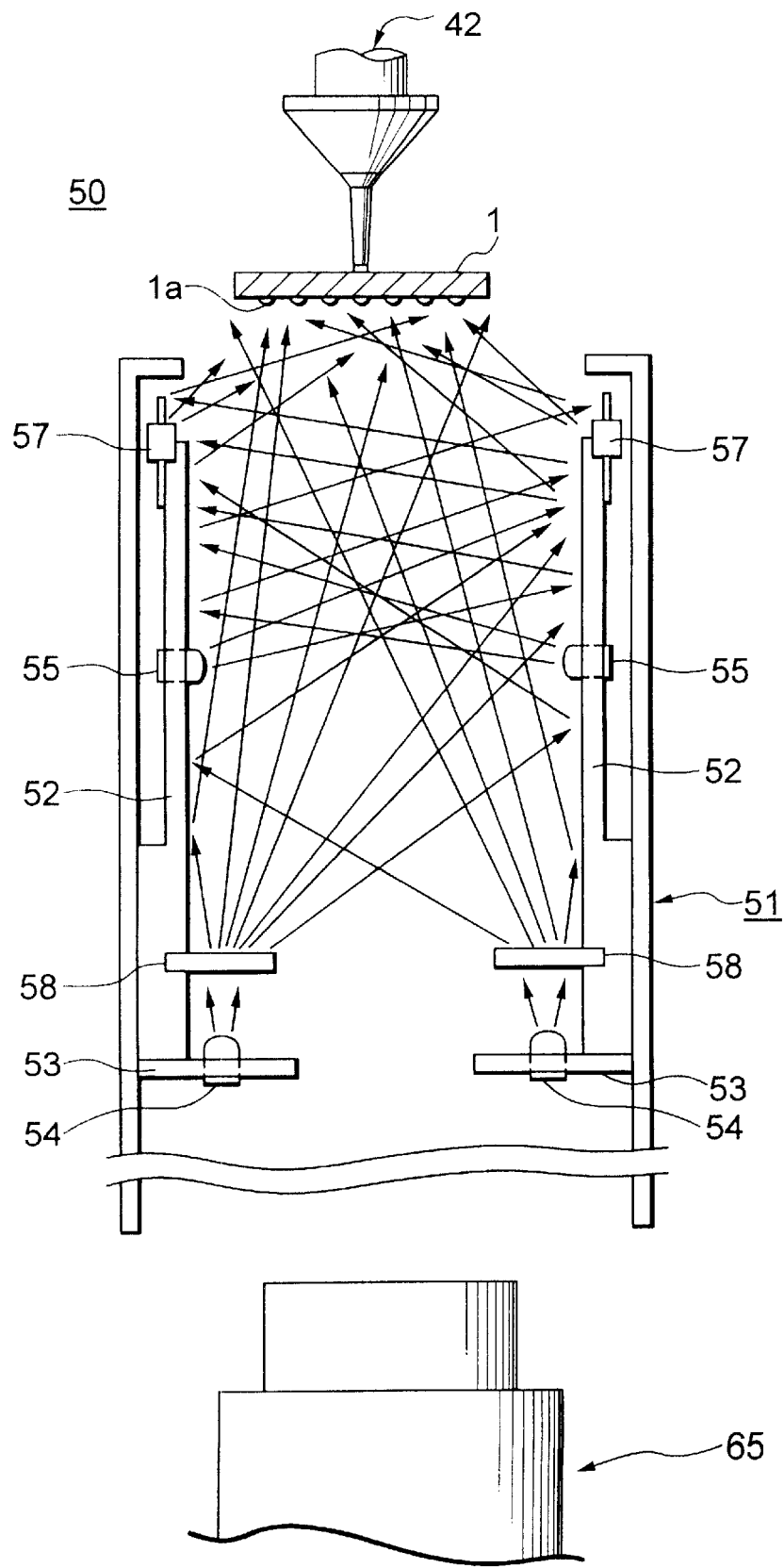
FIG. 9 is a sectional view of the component recognition unit while light is being radiated onto the BGA type semiconductor chip.

Firstly the control circuit 95 applies voltages to the LEDs 54, 55 and 57 to light them up as illustrated in FIG. 9. Since the distal ends of the LEDs 54, 55 and 57 have been trimmed as mentioned previously, light rays are emitted in the state of being diffused moderately from the LEDs 54, 55 and 57.

Some of the light rays emitted from the LEDs 54, 55 and 57 are further diffused while passing through the diffusion plate 58.

Since the first cylindrical member 52 covers those parts of the LEDs 57 which face the camera 65, no light is emitted toward the camera 65 from the LEDs 57. The light emitted from the uncovered parts of the LEDs 57 is radiated onto the to-be-mounted component throughout the whole circumference thereof.

The light rays diffused from the LEDs 54, 55 and 57 travel with being reflected at various angles and in various directions by the mirror-like inner surface of the first cylindrical member 52, while maintaining substantially the same intensity as that when emitted.

Thus, the light rays having a high directivity are radiated uniformly onto the semiconductor chip 1. The light rays reflected from the semiconductor chip 1 enter the camera 65.

The control circuit 95 instructs the camera 65 to photograph the to-be-mounted component. The camera 65 takes in the light reflected from the semiconductor chip 1 and performs the photoelectric conversion of the light, thus taking in an image of the semiconductor chip 1. Thereafter, the camera 65 supplies the image to the control circuit 95.

Employing a technique such as pattern matching or the like, the control circuit 95 compares the image of the semiconductor chip 1, supplied from the camera 65, with the correct image of the semiconductor chip 1 which has been stored in advance in the storage circuit 90. By this comparison, the control circuit 95 detects any positional deviation $\Delta x$, $\Delta y$, posture (rotational angle $\theta$) and any defect in the held semiconductor chip 1.

In the case where the control circuit 95 has detected any defect in the semiconductor chip 1, the control circuit 95 disposes the semiconductor chip 1 in a collecting box arranged in a predetermined position.

In the case where the control circuit 95 has detected no defect in the semiconductor chip 1, the control circuit 95 rotates the rotational motor 44 cancel the rotational angle $\theta$. Then, the control circuit 95 corrects the position of the nozzle 42 by the amount $-\Delta x, -\Delta y$ relative to the target position, and thereafter mounts the semiconductor chip 1 on the substrate 2 (in actual fact, the correction of any positional deviation of the substrate 2 is also performed, but its explanation will not be made herein to facilitate understanding, because such a correction is not directly connected with the present invention).

According to the component mounting apparatus 100 structured as above, the to-be-mounted component can be mounted in the appropriate position on the substrate 2, regardless of any positional deviation and rotation occurring at the time of the suction.

Furthermore, since a large number of LEDs 54, 55 and 57, having the trimmed distal ends and forming the light sources of the illuminators 51, are arranged in the circumferential direction, the light emitted from the LEDs 54, 55 and 57 is diffused over a wide region.

Moreover, because the inner surface of the first cylindrical member 52 is a mirror-like surface, the light emitted from the LEDs 54, 55 and 57 travels while being reflected on the inner surface of the first cylindrical member 52, and is uniformly radiated with a high directivity onto the to-be-mounted component. This permits the camera 65 to take an image in which the contrast between the semiconductor chip 1 and its background (any areas other than the semiconductor chip 1 within the scope of the camera 65, for example, the lower surfaces of the work head 41 and the nozzle 42) is high. Further, the images of the electrodes are clear and clearly distinguishable from their surrounding areas.

Figure 10:
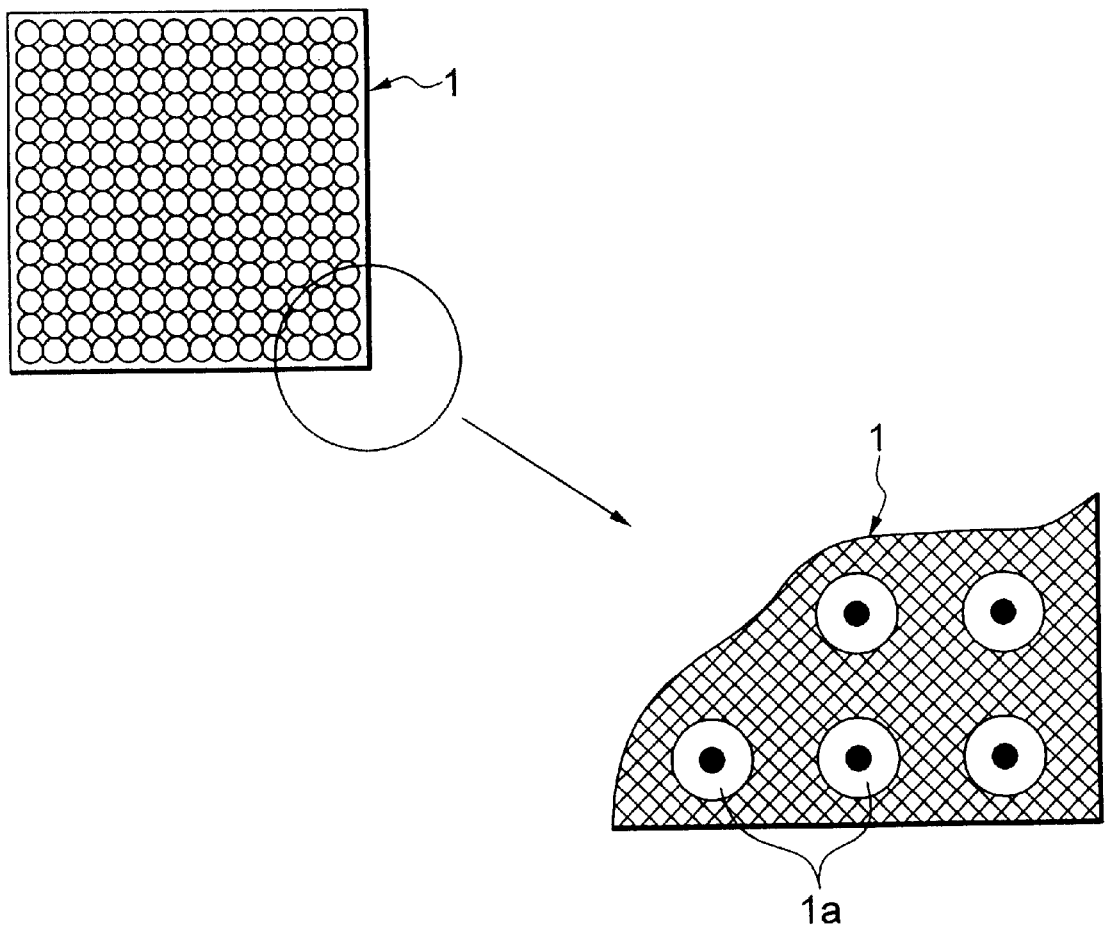
FIG. 10 is a diagram exemplifying a photographed image of the BGA type semiconductor chip.

FIG. 10 exemplifies an image photographed by the camera 65 while the semiconductor chip 1 of BGA type, in which a large number of ball-shaped electrodes have been formed on the lower surface of the chip, is being illuminated with the light emitted from the illuminators 51.

According to the illuminators 51 of this embodiment, the light emitted from the LEDs 57 arranged in a circle is radiated onto the semiconductor chip 1 throughout the whole circumference of the chip 1, as shown in FIG. 9. Unnecessary light reflected from below is cut off by virtue of the covering of those parts of the LEDs 57 which face the camera. Furthermore, the ball-shaped electrodes 1a are photographed by the camera 65 in the state wherein they are glistening annularly (in a doughnut shape). In the case where one ball-shaped electrode has a damaged/broken part, the damaged/broken part appears as a shadow in a photograph. Thus, the presence or absence of any damaged/broken part, as well as the presence or absence of the ball-shaped electrodes, can be easily detected in addition to the position and posture of the semiconductor chip.

In order to confer the appropriate directivity on the illumination light, it is preferred that the ratio of the diameter (inner diameter) of the first cylindrical member 52 to the length thereof be about 3/12 to 10/12, for example; more desirably about 5/12 to 10/12, and more preferably about 7/12 to 9/12. It is also preferred that: the LEDs 52 be located at the upper end of the first cylindrical member 52; the LEDs 54 be located in a slightly higher level than an imaginary plane which halves the first cylindrical member 52 perpendicularly to the axis of the first cylindrical member 52; the LEDs 52 be located on the bottom 53; and the diffusion plate 58 be located between a group of LEDs 54 and a group of LEDs 52.

The data shown in FIG. 10 has been attained under the conditions wherein the first cylindrical member 52 was formed from an aluminum plate having relatively flat surfaces, and the ratio of the diameter to length of the first cylindrical member 52 was set at approximately 8/12. (More specifically, the inner diameter and length of the first cylindrical member were approximately 4 cm and 6 cm, respectively. The LEDs 57 were located approximately 4 cm away from the upper end of the first cylindrical member. The LEDs 54 were located approximately 25 cm away from the upper end of the first cylindrical member. The LEDs 52 were located on the bottom 53. The diffusion plate 58 was employed).

According to the illuminators 51, since the second cylindrical member 56 is detachable from and engageable with the first cylindrical member 52, the maintenance of the illuminators 51 is easy. Furthermore, the structure of the illuminators 51 is simple because the LEDs 57 serve also as a buckle.

Figure 11:
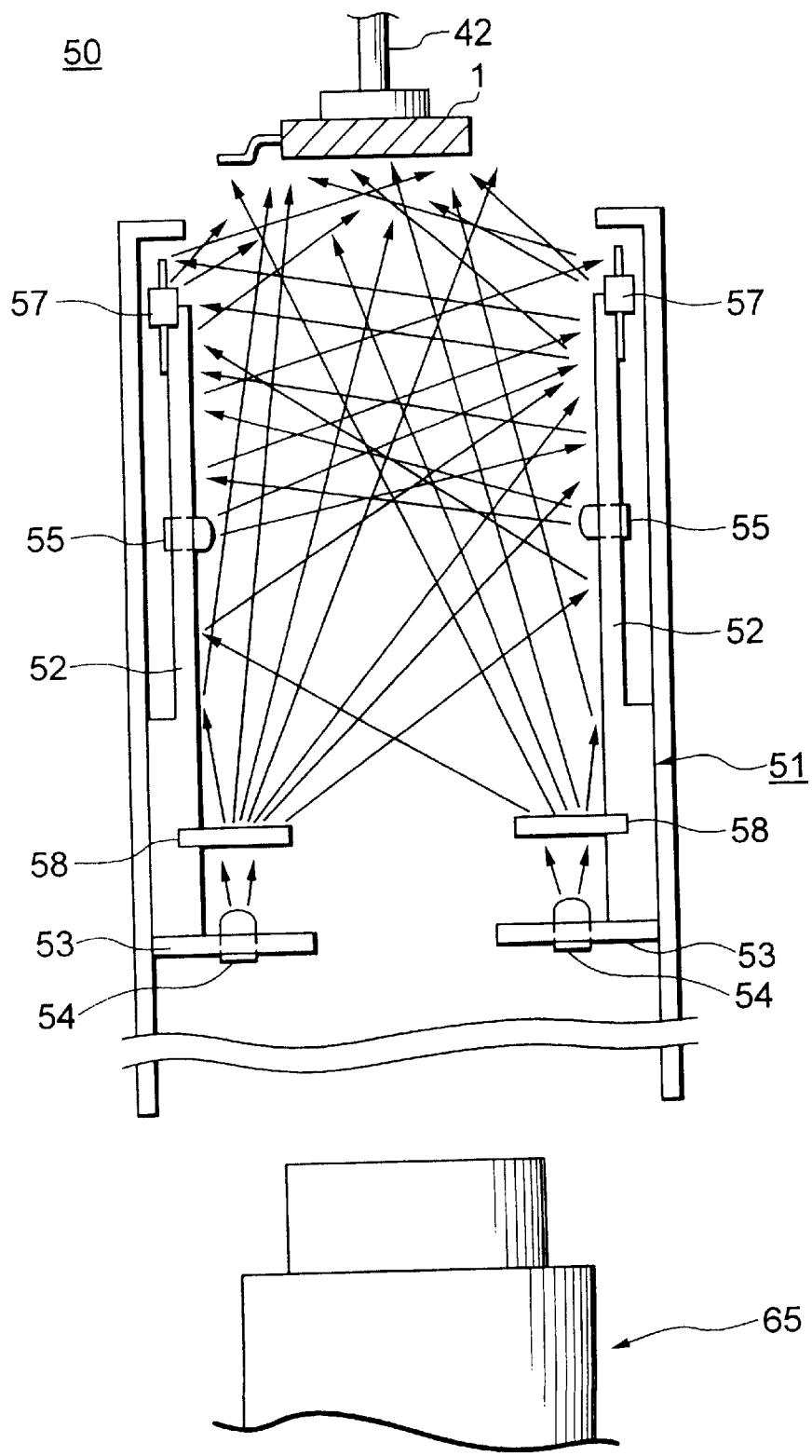
FIG. 11 is a sectional view of the component recognition unit while light is being radiated onto a semiconductor chip with solder plated leads.
Figure 12:
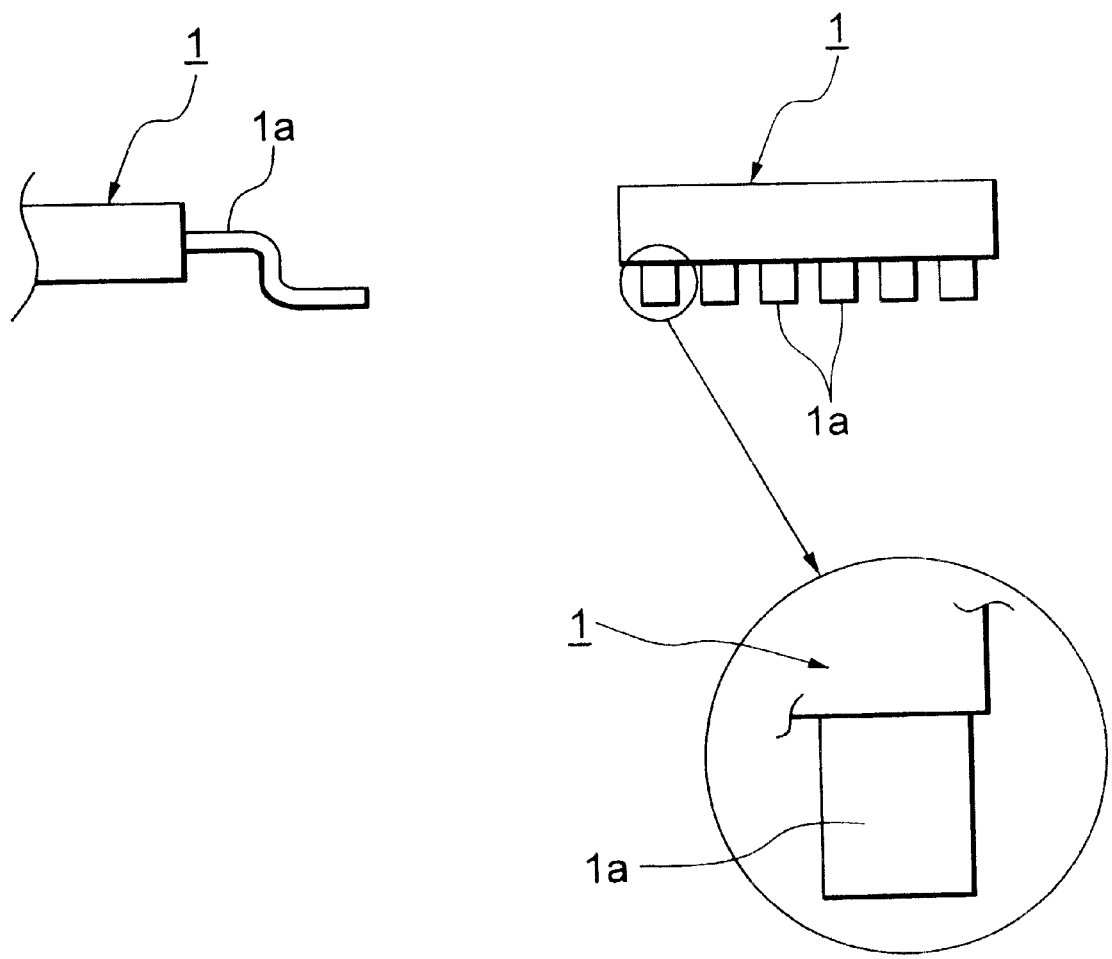
FIG. 12 is a diagram exemplifying a photographed image of the semiconductor chip with the solder plated leads while light is being radiated onto the semiconductor chip.
Figure 13:
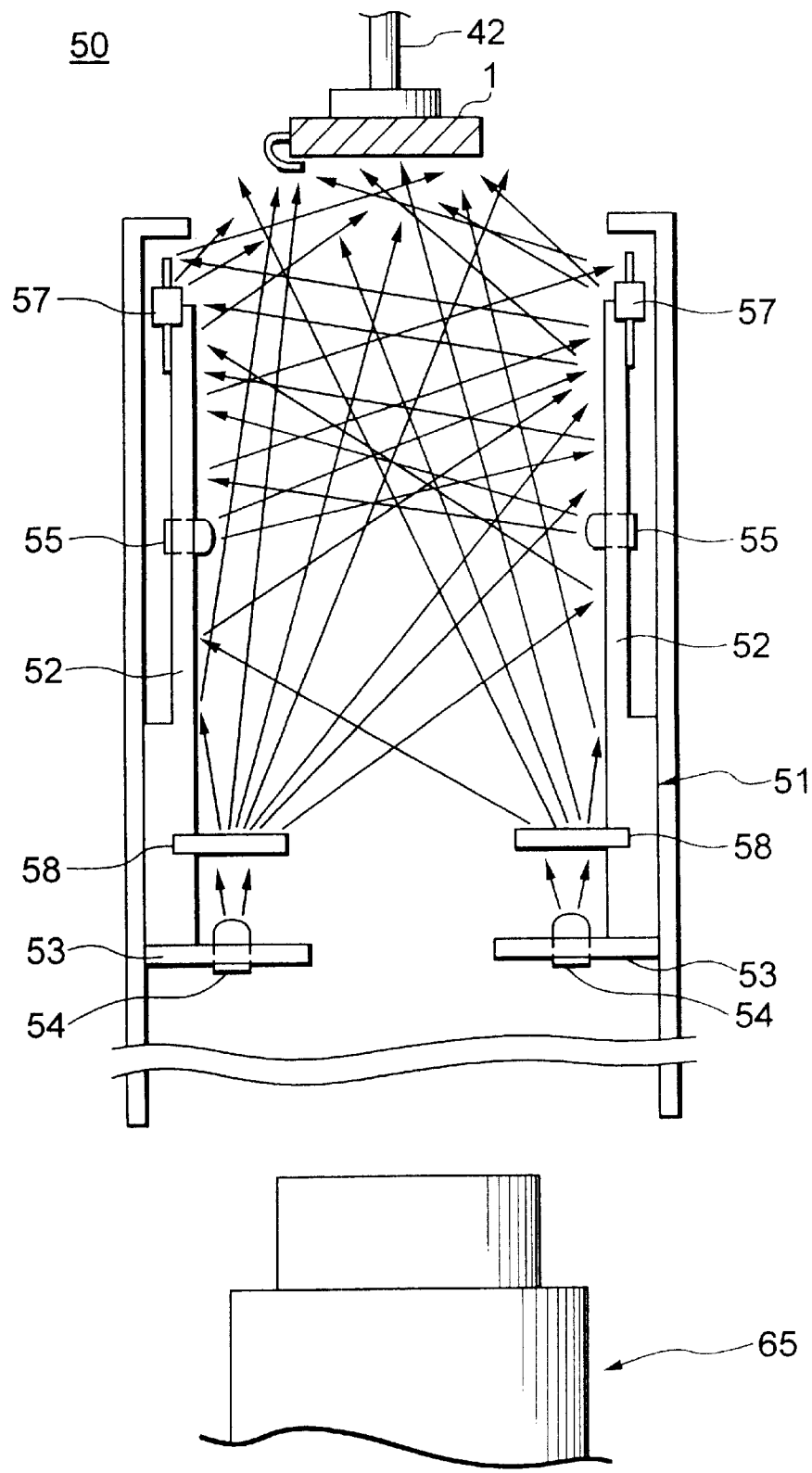
FIG. 13 is a sectional view of the component recognition unit while light is being radiated onto the semiconductor chip with the solder plated leads.
Figure 14A:
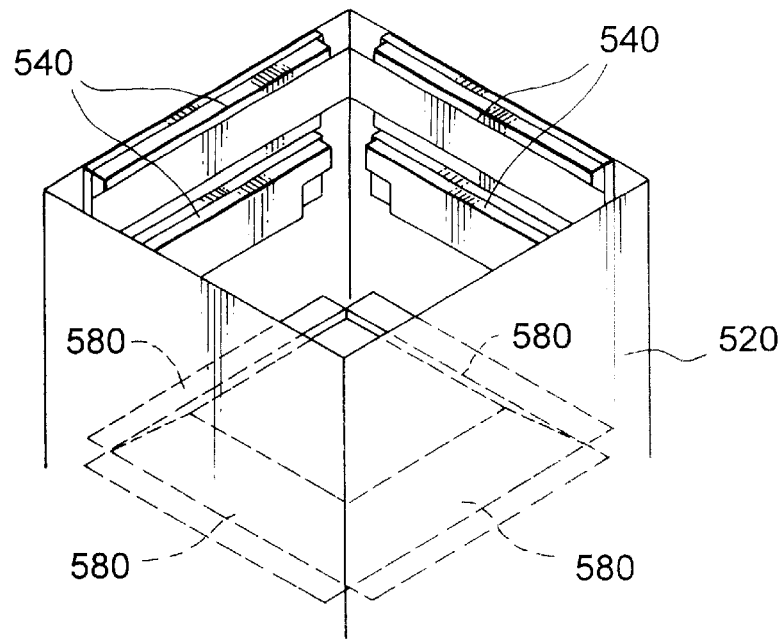
FIG. 14A is a partial perspective view of a conventional illuminator.
Figure 14B:
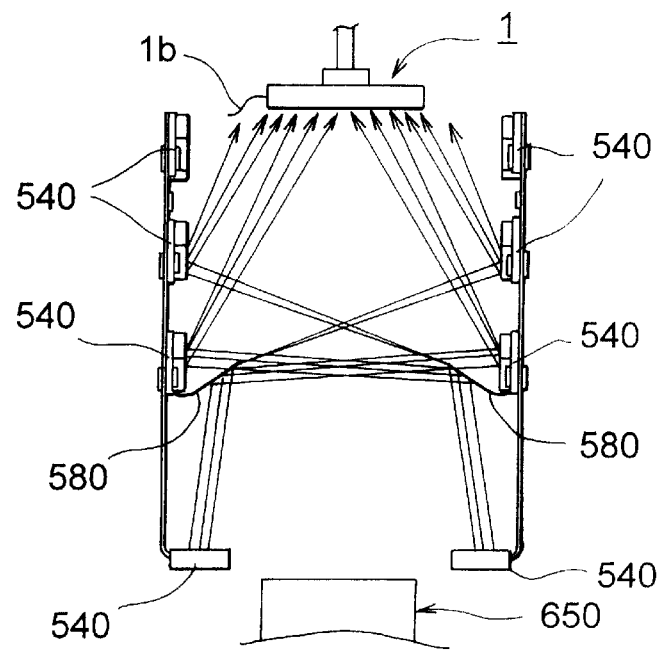
FIG. 14B is a sectional view of the conventional illuminator.
Figure 15:
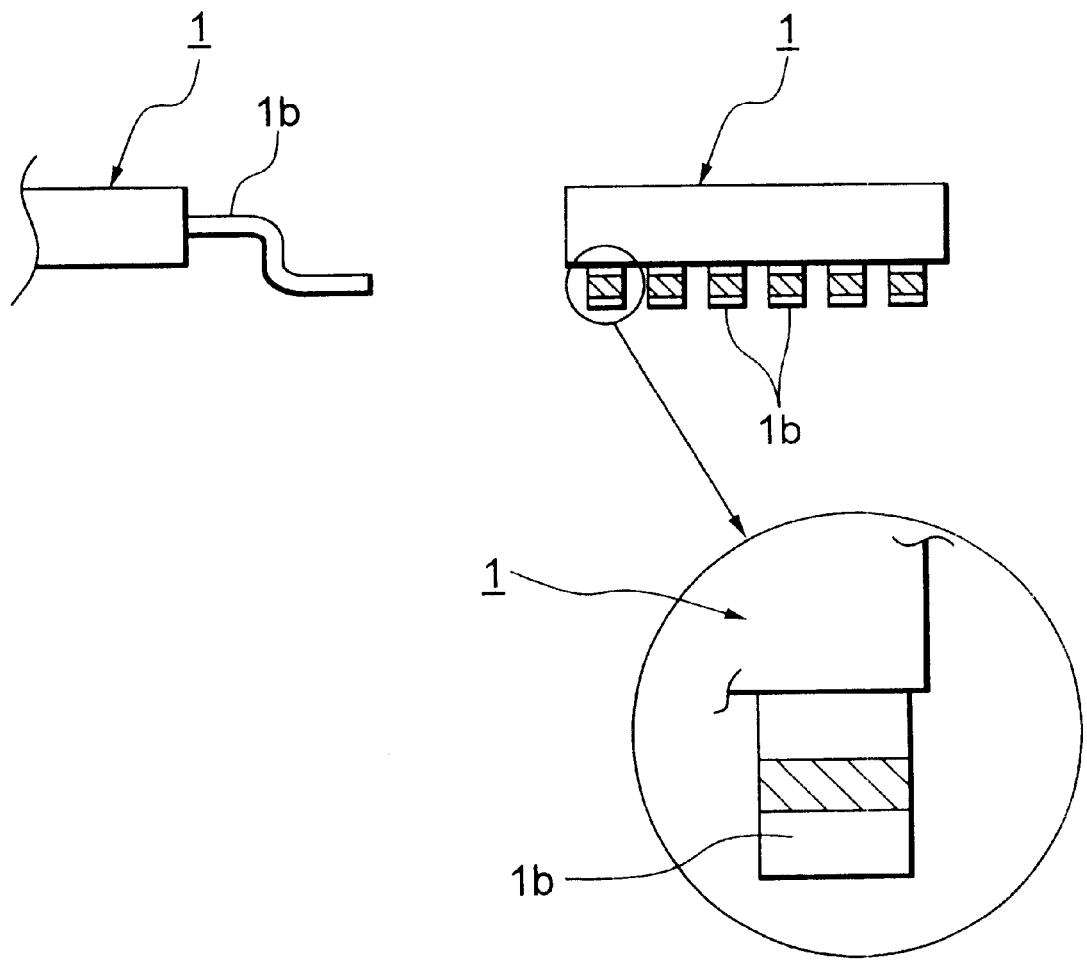
FIG. 15 is a diagram exemplifying a conventional photographed image of the semiconductor chip with the solder plated leads while light is being radiated onto the semiconductor chip.

The present invention is not limited to the above-described embodiment, and various modifications and applications are possible. For example, the to-be-mounted component 1 may be a semiconductor chip with solder plated lead, as illustrated in FIG. 11. And the structure of the nozzle 42 is not limited to the one disclosed in FIGS. 6A and 6B, as illustrated in FIG. 11. In the case where the to-be-mounted component 1 is a semiconductor chip with solder plated leads, the nonuniformity of brightness is prevented from occurring at any curved portions of the leads, as shown in FIG. 12. The to-be-mounted component 1 may be a semiconductor chip with leads having such a shape as that illustrated in FIG. 13.

Alternatively, the to-be-mounted component may be any one of electronic chips other than a semiconductor chip, or may be any one of chip-like parts other than the electronic chips. Furthermore, the mounting target is not limited to the semiconductor substrate.

The light sources of the illuminators 51 are not also limited to three groups of LEDs 54, 55 and 57. For example, two groups of LEDs excluding the group of LEDs 57 may be adopted. Alternatively, four groups of LEDs may be employed. The arrangement of the LEDs is also arbitrary, and the LEDs may be arranged in random positions, or may be arranged vertically (in parallel with the axis of the first cylindrical member 52).

Furthermore, the light sources are not limited to the LEDs which emit red light, and may emit light in any other color. Alternatively, the light sources may be light emitters other than the LEDs. For example, a flexible EL (electroluminescent) panel may be adhered to the inner surface of the first cylindrical member 52 so that the entire inner surface can be used as a light source. Alternatively, the flat plate member 53 may comprise the EL panel.

Furthermore, a cross section of the first cylindrical member 52 is not limited to a circular cross section, and may be any other shape. The first cylindrical member 52 may be rectangular in cross section.

According to the present invention, as described above, the to-be-mounted component is appropriately illuminated with light. Moreover, the accuracy of detection of the position and posture of the to-be-mounted component is improved.

This application is based on Japanese Patent Application No. H10-290491 filed Oct. 13, 1998, including specification, claims, drawings and summary. The disclosure of the above Japanese Patent Application is incorporated herein by reference in its entirety.

What is claimed is:

1. An illuminator for illuminating a to-be-mounted component with light, comprising:

light sources; and a reflector including a cylindrical member with a mirror-like inner surface by which light emitted from said light sources is reflected and radiated onto the to-be-mounted component, wherein:

said cylindrical member has a first end and a second end; and said light sources include:

first light sources forming a first light source group and arranged at the first end of said cylindrical member which is closer to the to-be-mounted component than the second end of said cylindrical member, second light sources forming a second light source group and arranged at the second end of said cylindrical member, and third light sources forming a third light source group and arranged between the first and second ends of said cylindrical member.

2. The illuminator according to claim 1, wherein the inner surface of said cylindrical member reflects the light emitted from said light sources and radiates light having a directivity, onto the to-be-mounted component.

3. The illuminator according to claim 1, wherein:

said cylindrical member leads, to the to-be-mounted component, the light emitted from said light sources, while reflecting the light by said inner surface; and said light sources are arranged inside said cylindrical member and emit light in an inner space defined by said cylindrical member.

4. The illuminator according to claim 1, wherein:

said cylindrical member is circular in cross section; and said first, second and third light sources are arranged in a circumferential direction of said cylindrical member.

5. The illuminator according to claim 1, wherein said cylindrical member covers parts of said first light sources which face the second end of said cylindrical member, in order to prevent light from being emitted toward the second end of said cylindrical member from said first light sources.

6. The illuminator according to claim 1, wherein:

said cylindrical member has a bottom which covers at least a part of an opening at the second end of said cylindrical member; and said second light sources are arranged on said bottom.

7. The illuminator according to claim 6, wherein a flat plate member which diffuses light emitted from said second light sources is arranged almost perpendicular to an axis of said second cylindrical member and between the second light source group comprising said second light sources and the third light source group comprising said third light sources.

8. The illuminator according to claim 1, wherein a flat plate member which diffuses light emitted from said second light sources is arranged almost perpendicular to an axis of said second cylindrical member and between the second light source group comprising said second light sources and the third light source group comprising said third light sources.

9. The illuminator according to claim 1, wherein said first light sources are detachably arranged at said reflector.

10. The illuminator according to claim 1, wherein at least one of the first light source group comprising said first light sources, the second light source group comprising said second light sources and the third light source group comprising said third light sources is a group of LEDs having distal ends trimmed to emit diffused illumination light.

11. An illuminator for illuminating a to-be-mounted component with light, comprising:

light sources; and a reflector including a cylindrical member with a mirror-like inner surface by which light emitted from said light sources is reflected and radiated onto the to-be-mounted component, wherein said light sources include:

first light sources forming a first light source group and arranged in a circle at the upper end of said cylindrical member;

second light sources forming a second light source group and arranged in a circle at the lower end of said cylindrical member; and third light sources forming a third light source group and arranged in a circle between the upper and lower ends of said cylindrical member.

12. The illuminator according to claim 11, wherein:

said cylindrical member has a bottom which covers at least a part of an opening at the second end of said cylindrical member; and said second light sources are arranged on said bottom.

13. The illuminator according to claim 11, wherein a flat plate member which diffuses light emitted from said second light sources is arranged almost perpendicular to an axis of said second cylindrical member and between the second light source group comprising said second light sources and the third light source group comprising said third light sources.

14. A component mounting apparatus comprising a head and illuminators, and which causes said head to suck up and hold a to-be-mounted component, causes said illuminators to illuminate the to-be-mounted component with light, detects a posture and position of the to-be-mounted component, controls said head in accordance with the detected posture and position of the to-be-mounted component, and mounts the to-be-mounted component held by said head in a predetermined position, each of said illuminators comprising:

light sources; and a reflector including a cylindrical member with a mirror-like inner surface by which light emitted from said light sources is reflected and radiated having a predetermined directivity onto the to-be-mounted component, wherein:

said cylindrical member has an upper end and a lower end; and said light sources include:

first light sources forming a first light source group and arranged in a circle at the upper end of said cylindrical member;

second light sources forming a second light source group and arranged in a circle at the lower end of said cylindrical member; and third light sources forming a third light source group and arranged in a circle between the upper and lower ends of said cylindrical member.

15. A component mounting apparatus comprising a head and illuminators, and which causes said head to suck up and hold a to-be-mounted component, causes said illuminators to illuminate the to-be-mounted component with light, detects a posture and position of the to-be-mounted component, controls said head in accordance with the detected posture and position of the to-be-mounted component, and mounts the to-be-mounted component held by said head in a predetermined position, each of said illuminators comprising:

light sources; and a reflector including a cylindrical member with a mirror-like inner surface by which light emitted from said light sources is reflected and radiated having a predetermined directivity onto the to-be-mounted component, wherein said cylindrical member covers parts of said first light sources which face the lower end of said cylindrical member, in order to prevent light from being emitted toward the lower end of said cylindrical member from said first light sources.

16. A component mounting apparatus comprising a head and illuminators, and which causes said head to suck up and hold a to-be-mounted component, causes said illuminators to illuminate the to-be-mounted component with light, detects a posture and position of the to-be-mounted component, controls said head in accordance with the detected posture and position of the to-be-mounted component, and mounts the to-be-mounted component held by said head in a predetermined position, each of said illuminators comprising:

light sources; and a reflector including a cylindrical member with a mirror-like inner surface by which light emitted from said light sources is reflected and radiated having a predetermined directivity onto the to-be-mounted component, wherein at least one of the first light source group comprising said first light sources, the second light source group comprising said second light sources and the third light source group comprising said third light sources is a group of LEDs having distal ends trimmed to diffuse illumination light.

17. A component mounting apparatus comprising a head and illuminators, and which causes said head to suck up and hold a to-be-mounted component, causes said illuminators to illuminate the to-be-mounted component with light, detects a posture and position of the to-be-mounted component, controls said head in accordance with the detected posture and position of the to-be-mounted component, and mounts the to-be-mounted component held by said head in a predetermined position, each of said illuminators comprising:

light sources; and a reflector including a cylindrical member with a mirror-like inner surface by which light emitted from said light sources is reflected and radiated having a predetermined directivity onto the to-be-mounted component, wherein:

said head comprises a nozzle, and said nozzle comprises a conic reflector which reflects lights, which are irradiated onto said nozzle by said illuminator, so that the direction of the reflected lights differs from the direction from said illuminator to said reflector.

18. A plurality of illuminators, used in a component mounting apparatus comprising a head which sucks up and holds a to-be-mounted component, for illuminating the to-be-mounted component held by said head with light, each of said plurality of illuminators comprising:

a cylindrical member with a mirror-like inner surface formed to facilitate light reflection and by which light is reflected and radiated having a directivity onto the to-be-mounted component;

a flat plate member having an aperture formed in a center thereof and covering a periphery of an opening at one end of said cylindrical member;

LEDs arranged in a circle along the periphery of said opening;

a ring-shaped semitransparent diffusion plate which diffuses light emitted from said LEDs;

LEDs arranged in a circle along a circumferential direction of said cylindrical member so as to be located on a lengthwise middle part of the inner surface of said cylindrical member;

an engagement portion engaged with said cylindrical member, and

LEDs arranged in a circle along a circumferential direction of said engagement portion and having distal ends trimmed substantially coplanar with the inner surface of said cylindrical member.

19. An illuminator for illuminating a to-be-mounted component with light, comprising:

light sources; and a reflector including a cylindrical member with a mirror-like inner surface by which light emitted from said light sources is reflected and radiated onto the to-be-mounted component, wherein said cylindrical member is circular in cross section.

20. A component mounting apparatus comprising a head and illuminators, and which causes said head to suck up and hold a to-be-mounted component, causes said illuminators to illuminate the to-be-mounted component with light, detects a posture and position of the to-be-mounted component, controls said head in accordance with the detected posture and position of the to-be-mounted component, and mounts the to-be-mounted component held by said head in a predetermined position, each of said illuminators comprising:

light sources; and a reflector including a cylindrical member with a mirror-like inner surface by which light emitted from said light sources is reflected and radiated having a predetermined directivity onto the to-be-mounted component, wherein said cylindrical member is circular in cross section.

21. A component mounting apparatus comprising a head and illuminators, and which causes said head to suck up and hold a to-be-mounted component, causes said illuminators to illuminate the to-be-mounted component with light, detects a posture and position of the to-be-mounted component, controls said head in accordance with the detected posture and position of the to-be-mounted component, and mounts the to-be-mounted component held by said head in a predetermined position, each of said illuminators comprising:

light sources; and a reflector including a cylindrical member with a mirror-like inner surface by which light emitted from said light sources is reflected and radiated having a predetermined directivity onto the to-be-mounted component, wherein:

said cylindrical member comprises a first end and a second end;

said light sources include:

first light sources forming a first light source group and arranged at the first end of said cylindrical member which is closer to the to-be-mounted component than the second end of said cylindrical member, second light sources forming a second light source group and arranged at the second end of said cylindrical member, and third light sources forming a third light source group and arranged between the first and second ends of said cylindrical member, said cylindrical member is circular in cross section; and said first, second and third light sources are arranged in a circumferential direction of said cylindrical member.

22. A component mounting apparatus comprising a head and illuminators, and which causes said head to suck up and hold a to-be-mounted component, causes said illuminators to illuminate the to-be-mounted component with light, detects a posture and position of the to-be-mounted component, controls said head in accordance with the detected posture and position of the to-be-mounted component, and mounts the to-be-mounted component held by said head in a predetermined position, each of said illuminators comprising:

light sources; and a reflector including a cylindrical member with a mirror-like inner surface by which light emitted from said light sources is reflected and radiated having a predetermined directivity onto the to-be-mounted component, wherein:

said cylindrical member comprises a first end and a second end;

said light sources include first light sources forming a first light source group and arranged at the first end of said cylindrical member which is closer to the to-be-mounted component than the second end of said cylindrical member, second light sources forming a second light source group and arranged at the second end of said cylindrical member, and third light sources forming a third light source group and arranged between the first and second ends of said cylindrical member, and a diffusion member which diffuses light emitted from said second light sources is arranged between the second light source group comprising said second light sources and the third light source group comprising said third light sources.

23. An illuminating method for illuminating a to-be-mounted component, sucked up and held by a head of a component mounting apparatus, with light emitted from illuminators, in order to recognize a posture and position of the to-be-mounted component through use of a camera, said method comprising the steps of:

reflecting light emitted from at least one light source by a mirror-like inner surface of a cylindrical member;

radiating the light, reflected having a directivity by the inner surface of said cylindrical member, onto the to-be-mounted component, and emitting light from light sources, wherein:

said cylindrical member comprises a first end and a second end;

said light sources include:

first light sources forming a first light source group and arranged at the first end of said cylindrical member which is closer to the to-be-mounted component than the second end of said cylindrical member, second light sources forming a second light source group and arranged at the second end of said cylindrical member, and third light sources forming a third light source group and arranged between the first and second ends of said cylindrical member;

said cylindrical member is circular in cross section; and said first, second and third light sources are arranged in a circumferential direction of said cylindrical member.

24. The illuminating method according to claim 23, wherein in said radiating step, light is prevented from being emitted toward the second end of said cylindrical member from said first light sources by covering parts of said first light sources which face the second end of said cylindrical member.

25. The illuminating method according to claim 23, wherein in said reflecting step, light emitted from said second light sources is diffused by a diffusion member which is arranged between the second light source group comprising said second light sources and the third light source group comprising said third light sources.

* * * * *